United States Patent
Hill et al.

(10) Patent No.: US 6,823,870 B1
(45) Date of Patent: Nov. 30, 2004

(54) PATIENT SAFETY STRAPS

(75) Inventors: Darrell G. Hill, Edina, MN (US); Robert T. Horan, Fountain Hills, AZ (US)

(73) Assignee: D. G. Hill Associates, Edina, MN (US)

(*) Notice: Subject to any disclaimer, the term of this patent is extended or adjusted under 35 U.S.C. 154(b) by 0 days.

(21) Appl. No.: 10/115,878

(22) Filed: Apr. 4, 2002

Related U.S. Application Data

(60) Provisional application No. 60/281,654, filed on Apr. 5, 2001.

(51) Int. Cl.[7] .............................................. A61B 19/00
(52) U.S. Cl. ...................................... 128/869; 128/876
(58) Field of Search ................................. 128/869, 874, 128/875, 876; 602/19

(56) References Cited

U.S. PATENT DOCUMENTS

| | | | |
|---|---|---|---|
| 3,939,829 A | 2/1976 | Spann | 128/133 |
| 3,970,079 A * | 7/1976 | Gaylord | 602/19 |
| 4,108,170 A | 8/1978 | Spann | 128/134 |
| 4,127,120 A | 11/1978 | Applegate | 128/134 |
| 4,396,013 A | 8/1983 | Hasslinger | 128/133 |
| 4,584,993 A | 4/1986 | Nelson | 128/77 |
| 4,662,517 A * | 5/1987 | Wirth | 206/388 |
| 4,899,763 A | 2/1990 | Sebastian et al. | 128/878 |
| 5,048,134 A | 9/1991 | Dennill et al. | 51/82 |
| 5,492,133 A | 2/1996 | McVicker | 128/876 |
| 5,503,894 A * | 4/1996 | Brown | 428/128 |
| 5,664,581 A | 9/1997 | Ashley | 128/876 |
| 6,053,169 A | 4/2000 | Hunt | 128/876 |

* cited by examiner

*Primary Examiner*—Michael Brown
(74) *Attorney, Agent, or Firm*—Patterson, Thuente, Skaar & Christensen, P.A.

(57) ABSTRACT

A device for restraining patients using specially designed straps in various lengths and widths that positively and securely secure a portion or all of a patient's anatomy so as to facilitate securing patients while minimizing trauma and bruising to the patient's body during surgical procedures or in transportation in medical facilities. The invention includes a device with a length of non-allergenic fabric having a soft patient engaging surface and an opposed patient non-engaging surface, first and second opposed ends, opposed edges, and a fastener associated with the length for fastening the device to itself, the edges of the fabric being folded over to present a rolled side margin having a continuously smooth and curved margin face, with the device being sanitizable and reusable, thereby hygienically for minimizing trauma to the mobility limited body portion.

26 Claims, 6 Drawing Sheets

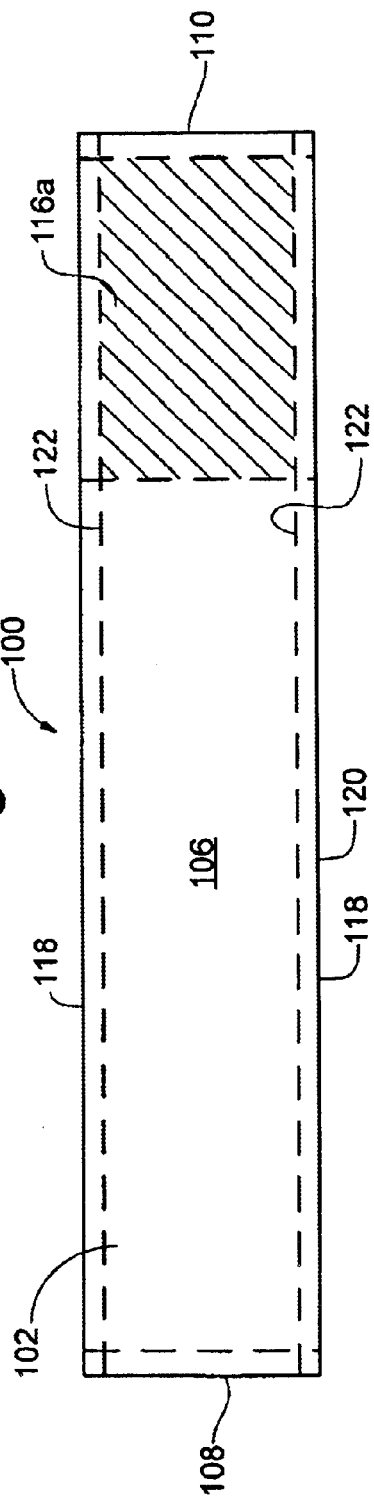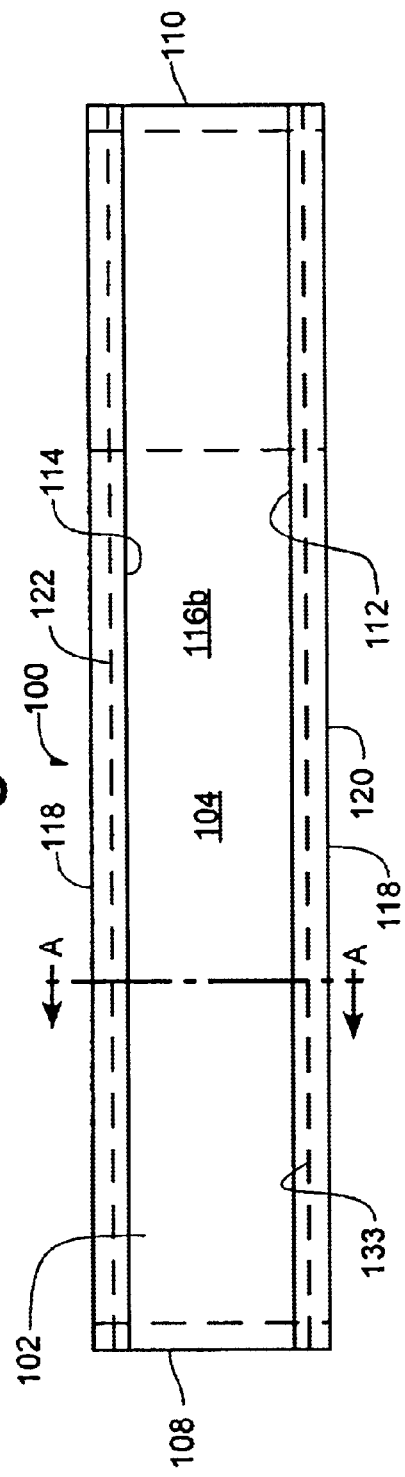

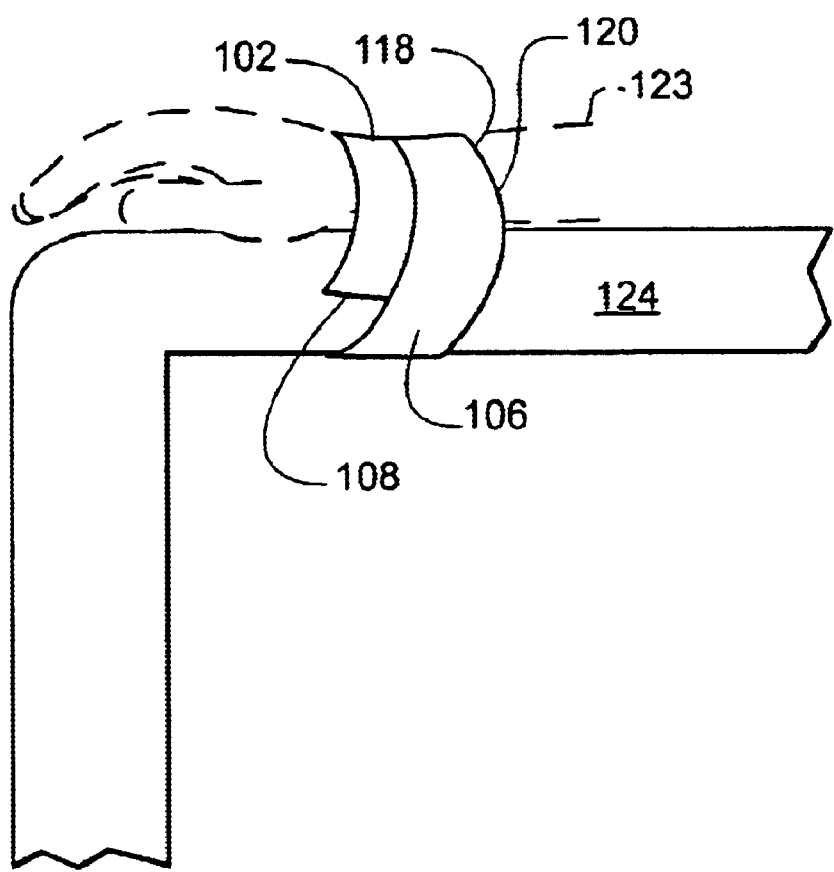

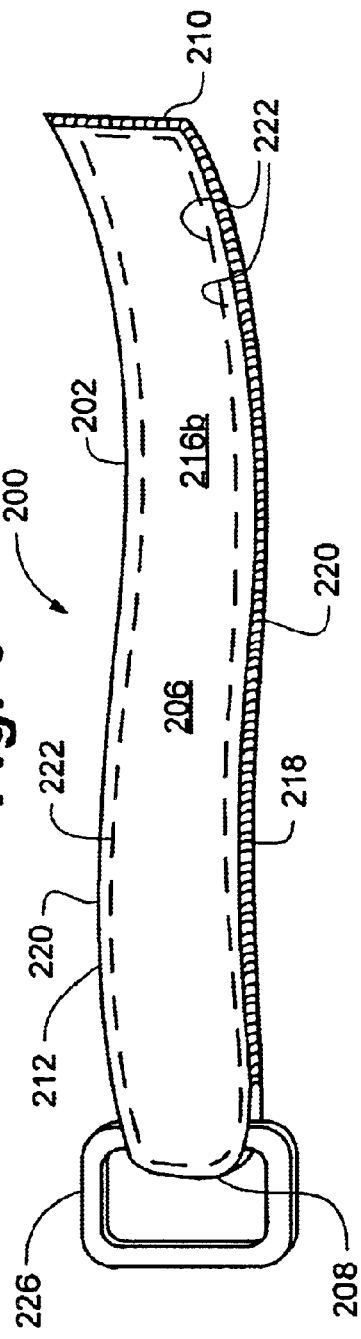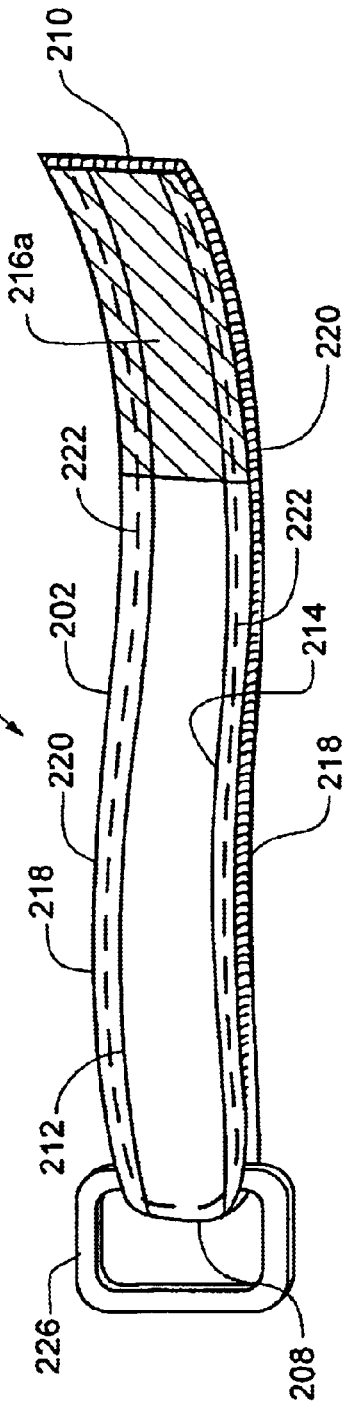

US 6,823,870 B1

PATIENT SAFETY STRAPS

RELATED APPLICATIONS

This application claims priority to U.S. patent application No. 60/281,654 entitled "PATIENT SAFETY STRAP", filed Apr. 5, 2001, which is hereby incorporated herein by reference.

FIELD OF THE INVENTION

The invention relates to devices for restraining patients. More particularly, it relates to specially designed straps that positively and securely secure a portion or all of a patient's anatomy, for facilitating patient immobilization, while at the same time minimizing trauma and bruising to the patient's body.

BACKGROUND

Straps are ubiquitous in hospitals and medical settings and have an impact on the quality of patient care. Medical personnel must use straps to secure patients so that they do not fall off of procedure tables, gurneys, or stretchers in treatment areas. Straps are also used to position a patient for treatment; for instance, for holding an arm securely in place for receipt of an intravenous needle during surgery. Straps must be securable by medical personnel and effectively hold a patient in place on a gurney, a table, in a chair, or the like.

Although straps are commonly used, medical providers have done little to address the safety, quality, and ergonomic aspects of the straps that they use. It is common for patients that undergo surgery to awaken with welts, bruises, and broken skin around the areas where their body or limbs have been restrained. Injuries include damaged skin, capillaries, and veins. This problem is particularly acute for elderly patients because their skin and dermis is more fragile than that of younger persons and they recover more slowly. These problems are aggravated by the fact that patients' bare skin often encounters these straps because patients' bare skin must be exposed for medical access or sanitary reasons.

Conventional belt straps are characterized by buckles, fabrics that form sharp edges, and rough fabric. Moreover, conventional patient straps often have buckles or other fasteners with surfaces and shapes that resist sterilization and cannot be easily sanitized. Further, the materials of the straps themselves typically resist sanitization and forms. Thus the spread of infections through a hospital, which is a common problem, may be aggravated by conventional patient straps.

Some conventional straps are made from natural rubber that contains latex. Latex is a potent allergen that is typically restricted in hospitals so that extra processing steps that avoid or eliminate latex are required for hospital uses that contain latex straps.

Patient straps should be quickly and easily secured and unsecured. Medical personnel face significant challenges in handling weak or unconscious patients that need bodily support; fumbling with straps or buckles is awkward and increases the potential for injury to the patient or nurse or other medical personnel. Moreover, patient straps should be sanitizable by laundering, autoclaving, or chemical treatment. And patient straps should minimize harm to patients, even when contacting their bare skin.

SUMMARY OF THE INVENTION

The present invention addresses these problems. A preferred embodiment of the invention is a strap made of a soft material that has curved margins. The curved margins are in contrast to the corners that are found in a typical patient strap. The soft material is in contrast to conventional materials that cause discomfort to a patient, especially when contacting the bare skin. The strap preferably has no buckles but instead uses hook-and-loop fasteners and/or a hoop or hoops that interlock with the strap to secure it.

An embodiment of the invention is a restraining device that has a fabric length with a top and a bottom joined by at least one margin that is curved for at least a portion of the length of the margin. The bottom of the strap is preferably soft and is made of a soft pliable, fabric, or combination of the same. The device preferably incorporates hook-and-loop fasteners to help secure the strap. The device is preferably sanitizable by laundering, autoclaving, or chemical treatments such as anti-microbial disinfection.

An embodiment of the invention is a length of non-allergenic fabric having a soft patient engaging surface and an opposed patient non-engaging surface. The length has first and second opposed ends, opposed edges, and a fastener associated with the length, preferably for fastening the device to itself. The edges of the fabric are folded over to present a side margin having a smooth and curved face. The device is preferably sanitizable and reusable. So as to hygienically minimize trauma to the body portion that is restrained.

An embodiment of the invention is a method of restraining a patient by using a restraining device that has a fabric length with a top and a bottom joined by a margin that is curved for at least a portion of its length, and placing the bottom of the strap against the patient, and fastening the device to itself The method may include a step of sanitizing or sterilizing by laundering, autoclaving, irradiating, or chemically treating the device. The strap is preferably provided with a soft bottom. A method of making the strap includes making a curved margin of the strap by folding a material and creating a seam near an edge of the strap, a type of margin sometimes referred to as rolled.

Curved margins and soft materials reduce the injury and discomfort that patients experience when subjugated to the use of conventional straps. The use of hoops, hook-and-loop materials, and other fasteners allows for rapid and convenient use of the invention. The restraint devices of certain embodiments of the invention are conveniently sanitizable by laundering or autoclaving so that medical workers may conveniently maintain high hygienic standards and re-use the devices. The strap system is versatile and may be used with most patient supporting devices.

BRIEF DESCRIPTION OF THE FIGURES

FIG. 1 depicts a plan view of the patient non-engaging surface of an embodiment of the invention.

FIG. 2 depicts a bottom plan view of the patient engaging surface of the device depicted in FIG. 1.

FIG. 5 depicts subsequent steps in the method of use depicted in FIG. 4.

FIG. 6 depicts a plan view of the patient non-engaging surface of an alternative embodiment of the invention.

FIG. 7 depicts a bottom plan view of the patient engaging surface of the device depicted in FIG. 6.

DETAILED DESCRIPTION OF THE INVENTION

Figure 3:
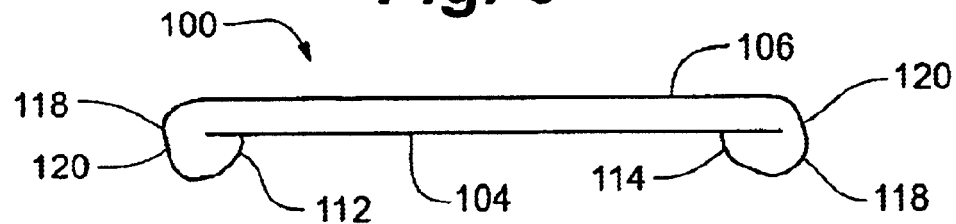
FIG. 3 depicts a cross-sectional view of the section A–A' indicated in FIG. 2.

A preferred embodiment is a device with a strap with a soft surface and curved margin that has a fastener for fastening the strap and securing the patient. Referring to FIGS. 1–5, a preferred embodiment of the device 100 has length 102 of fabric having patient engaging surface 104 and opposed patient non-engaging surface 106, first end 108 and second end 110, opposed edges 112, 114, and a fastener 116 associated with length 102 for fastening device 100 to itself, with edges 112, 114 of the fabric being folded over to present rolled side margin 118 having a continuously smooth and curved margin face 120. Seams 122 secure margins 118. The fastener hook portion 116a is part of a hook and loop fastener and reversibly attaches to patient engaging surface 104, which also serves as the loop portion 116b of the fastener.

Figure 4:
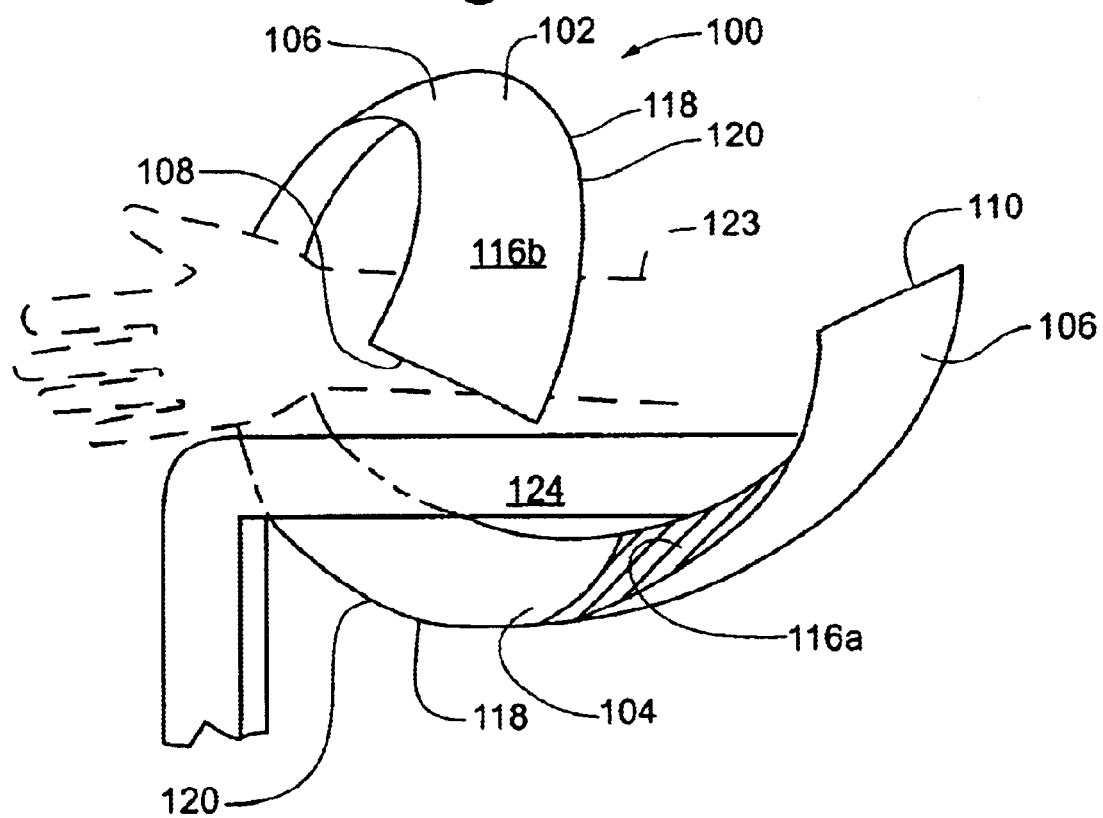
FIG. 4 depicts initial steps for using the device depicted in FIGS. 1–3 to secure a patient's limb to a structure.
Figure 8:
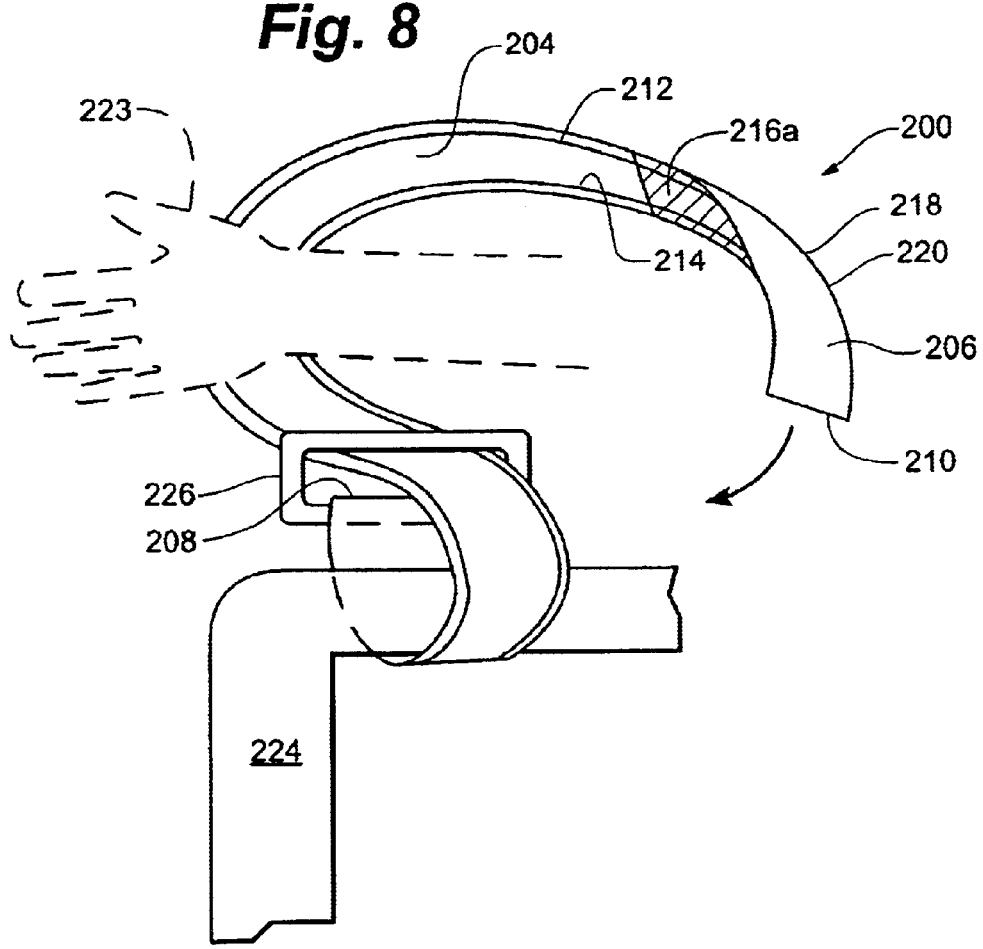
FIG. 8 depicts initial steps for using the device depicted in FIGS. 6 and 7 to secure a patient's limb to a structure.
Figure 9:
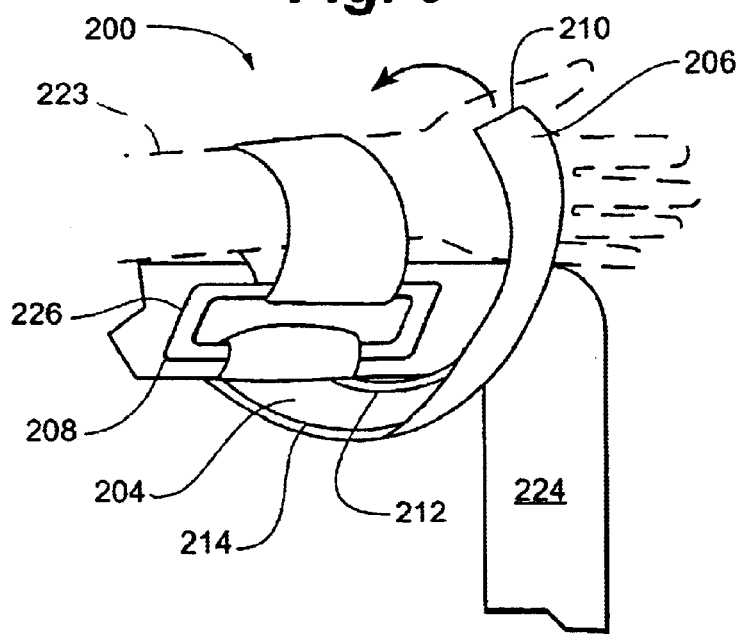
FIG. 9 depicts subsequent steps in the method of use depicted in FIG. 8.

In use, referring to FIGS. 4 and 5, length 102 of fabric is wrapped around body portion 123 of a patient and patient supporting structure 124 and fastened with hook and loop fastener 116a and 116b.

Another preferred embodiment is a device with a strap with a soft surface and rounded edges that has a fastener that includes a hoop for fastening the strap and securing the patient. Referring to FIGS. 6–9, device 200 has length 202 of fabric having patient engaging surface 204 and opposed patient non-engaging surface 206, first end 208 and second end 210, opposed edges 212, 214, and a fastener 216a, 216b associated with length 202 for fastening device 200 to itself, with edges 212, 214 of the fabric being folded over to present side margin 218 having a continuously smooth and curved margin face 220. Seams 222 secure margins 218. The fastener hook portion 216a is part of a hook and loop fastener and reversibly attaches to patient non-engaging surface 206, which also serves as the loop portion 216b of the fastener. Hoop 226 is associated with end 208.

In use, length 202 of device 200 is looped around patient supporting structure 224 by passing end 210 through hoop 226 and wrapping length 202 around patient's body portion 223 and fastening device 200 to itself by attaching hook portion 216a to patient non-engaging surface 206.

Figure 10:
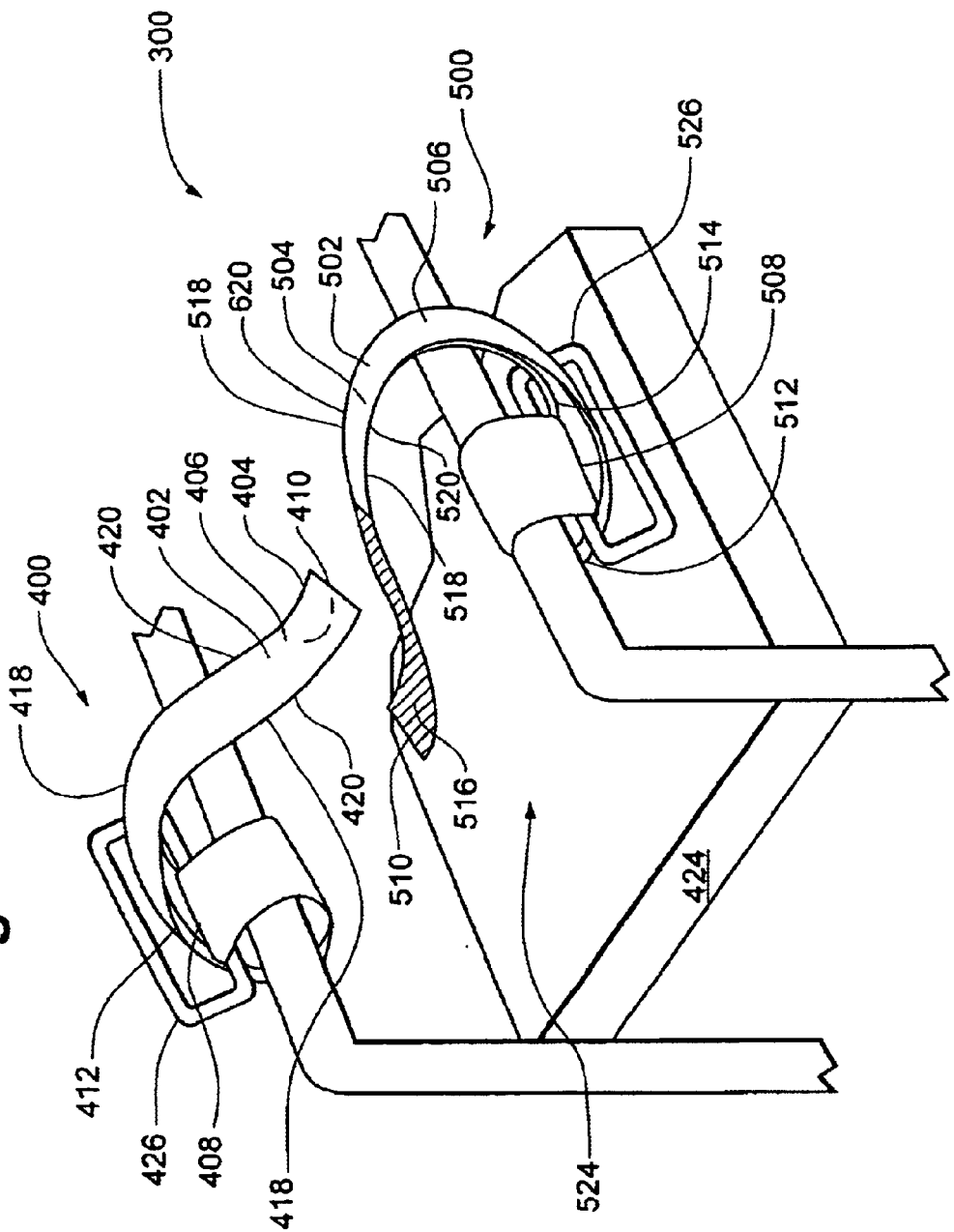
FIG. 10 depicts an alternative embodiment of the invention.

Another preferred embodiment of the invention is system 300, as shown in FIG. 10. System 300 has devices 400 and 500 that have a length 402, 502, a patient engaging surface 404, 504, an opposed patient non-engaging surface, 406, 506, first opposed end 408, 508, second opposed end 410, 510, opposed edges 412, 414 (not shown), 512, 514, and a fastener. The fastener is in the form of a hook material 516 associated with length 502 that fastens to length 402 which is made of a loop material on patient contacting side 410. Edges 412, 414 (not shown), 512, 514 of the fabric are folded over to present rolled side margins 418, 518 having a continuously smooth and curved margin face 420, 520. Seams 422, 522 (not shown) secure margins 418, 518. Hoops 426, 526 are associated with ends 408, 508.

In use, end 410, 510 are passed through hoops 426, 526 and tightened around structure 424. Ends 410, 510 are fastened securely around a patient in space 524 using a fastener of hook material 516 affixed to loop material on surface 410.

The strap system is adaptable to many applications, including patient supporting structures such as surgical and procedure tables in hospitals and ambulatory centers, gurneys, stretchers, transportation stretchers, wheel chairs, obstetrics tables, emergency room stretchers, ambulance stretchers, and emergency room facilities. Further, the strap system is adaptable to surgical table accessories such as arm boards, table attachments, intravenous therapy positioners, and all related table paraphernalia that demands the patients' limbs, body, arms, head, etc., to be secured with a strap that prevents unwanted movement.

The preferred materials for the device are non-allergenic. Such materials include polyesters, polyamides, cotton, and rubber materials that are latex-free. Fabrics made from natural and synthetic materials may be used. The fabrics are flexible and conform to the shape of the patient or patient support structure. Certain embodiments of the invention include a rigid member made of a plastic or metal. The hoops of certain embodiments are preferably made of a rigid plastic, e.g., nylon, polypropylene, polyethylene, polycarbonate, polystyrene, fluoropolymers, and other engineering plastics known to those skilled in these arts. Hoop is a broad term that includes round, circular, square, polygonal, and other shapes, that accept the passage of another part through themselves. Alternative plastic members that are flexible and elastic may be used. A most preferred fabric material is medical grade nylon tricot. An advantage of this material is that it becomes softer with repeated machine washings.

The preferred materials that are used for contacting the patient are soft in comparison with other products. Soft means that they seem softer to a majority of ordinary persons or clinical nurses that feel them with their hands and compare them to straps conventionally used on a procedure table or gurney, for example, straps sold by Devon™ Industries as Part Number 2020 in their United States Catalog "Positioning Plus System" issued in the year 1998.

The patient-engaging surface is preferably made with a soft, flexible material that is lightweight and flame-resistant. Not every portion of the device that is described as the patient-engaging surface is in contact with the patient during use and similarly, not every portion of the patient non-engaging surface is not in contact with the patient. These designations are for the convenience in describing the device. The device may be used in an enormous variety of configurations that dispose the surfaces in many ways not explicitly described herein.

The edges of a fabric used for making the device are preferably rolled over to make a margin having a margin face that is smooth and curved. Curved is a broad term that encompasses not only hemispherical shapes but other curved shapes, e.g., ellipses, parabolas, hyperbolas. The margin is preferably smoothly curved and not discontinuous and does not have sharp changes in direction. Other embodiments include a one-piece soft material where the edges are cut and rolled over to make a soft margin. Also, a length of material with bulging rounded edges may be made. Also a length of material may be made with a 360° soft fabric character with a soft margin as part of the material. Further, other materials may be introduced under the curved surface, for example a foam material that is sewn into the seam so that the margin has extra cushioning effects. A variety of margins are contemplated such as traditional, attached, rolled with the same material, and a one-piece material manufactured with a soft margin. Other embodiments have no exposed threads or stitches. Other alternative margins include unfinished edges and selvedge edges or margins.

A preferred means of making the curved margin is by folding and sewing a seam to secure the edges. An alternative involves securing the edges with bias or twill tape. Other alternatives include the use of adhesives, textile imprinting techniques, application of heat and the use of ultrasound. These methods for making curved margins are in contrast to a typical conventional process of using raw or uncut edges that have not be engineered to minimize injury.

The devices of the invention are preferably configured to be sanitizable and/or sterilizable. Sanitizable is a broad term that means to clean or disinfect and may include sterilization. Sterilize means to essentially kill all microorganisms. Laundering is a sanitization process. Autoclaving is a sanitization and a sterilization process that involves exposing the devices to steam and, typically, to elevated pressure, as is known to those skilled in the arts of hospital administration. Chemical treatment with bleaches, ammonia, bases, alcohols, and surfactants are examples of chemical processes for sanitization and/or sterilization. Treatment by irradiation and ethylene oxide are sterilization processes that may optionally be used with certain embodiments of the invention. These features allow the fasteners to be cleaned and even sterilized periodically and thoroughly.

The device has a fastener for fastening the device to itself or, alternatively, to a fixed structure. Suitable fasteners include a hook-and-loop system, snaps, a loop, ring, gripping means, pair of rings, strap, snap, collet, button, zipper, hook, tightening means, slack removing means, and other means known to those skilled in these arts. One or more parts could be used. The strap joining means could be variously placed at different portions of the strap, including one of the ends or in the middle, on the top or on the patient-contacting side. The fastener(s) could be variously placed at different portions of the length, including one of the ends or in the middle, or on either side.

Other alternative embodiments are included in the invention. Such embodiments include disposable versions of the straps. The straps may be made of lightweight durable material. Examples include polyurethane foams backed with nylon-based materials. Devices and systems that include disposable or removable coverings are contemplated. These embodiments are especially useful for preventing the spread of germs. The disposable coverings are removed after a patient has contacted them and new ones are put into place. Suitable materials for coverings are known to those skilled in these arts and include paper. Straps of various sizes and shapes are contemplated, including rectangular straps of four inches, three inches, and one-and-one-half inches. Pads may be incorporated into the straps. Pads are preferably made of lightweight resilient materials. Suitable materials include polyurethane foams and polyvinyl coverings. Stretching materials may be incorporated that are elastic so that the straps may be fit more snugly to the patient. Extra buckles, fasteners, tighteners, tightening arrangements, slip-and-grip devices, and ratchets may be included. Webbing or multiple strap systems may be used. Embodiments with separate materials such as tape or bias tape may be used. The bias tape may be incorporated into the edge of the hook-and-loop material. This product can be and is manufactured as a disposable product, for use in some situations where infection and contamination are of great concern.

The examples and embodiments described herein encompass only a small range of the number of possible embodiments of the invention and are not intended to limit the scope of the invention.

It is claimed:

1. A patient restraining device for temporarily, safely, and comfortably limiting the mobility of a body portion of a human patient relative to a patient supporting structure, comprising:

a length of non-allergenic fabric having a soft patient engaging surface and an opposed patient non-engaging surface, first and second opposed ends, opposed edges, and a fastener associated with the length for fastening the device to itself and the table and/or stretcher, the edges of the fabric being folded over to present a rolled side margin having a continuously smooth and curved margin face, with the device being sanitizable and reusable, thereby hygienically minimizing trauma to the mobility limited body portion, wherein the device comprises a rigid nylon plastic hoop.

2. The device of claim 1 wherein the fastener is a hook-and-loop fastener.

3. The device of claim 1 wherein the hook portion of the hook-and-loop fastener is disposed on the patient-engaging side.

4. The device of claim 1 wherein the device is sanitizable by laundering or autoclaving.

5. A method of restraining a patient relative to a patient supporting structure, the method comprising:

providing a length of non-allergenic fabric having a soft patient engaging surface and an opposed patient non-engaging surface, first and second opposed ends, opposed edges, and a fastener associated with the length for fastening the device to itself, the edges of the fabric being folded over to present a side margin having a continuously smooth and curved margin face, with the device being sanitizable and reusable, placing the patient non-engaging surface against the patient, fastening the device to itself, and further comprising fastening the device to itself by passing a first end of a strap through a hoop affixed to the length and fastening a portion of the length to another portion of the device using a hook-and-loop fastener.

6. The method of claim 5 further comprising fastening the device to itself by fastening a hook-and-loop fastener.

7. The method of claim 5 further comprising laundering the device.

8. The method of claim 5 further comprising autoclaving the device.

9. A method of restraining a patient relative to a patient supporting structure, the method comprising:

providing a length of non-allergenic fabric having a soft patient engaging surface and an opposed patient non-engaging surface, first and second opposed ends, opposed edges, and a fastener associated with the length for fastening the device to itself, the edges of the fabric being folded over to present a side margin having a continuously smooth and curved margin face, with the device being autoclavable, placing the patient non-engaging surface against the patient, and fastening the device to itself.

10. The method of claim 9 wherein the fastener comprises a hook-and-loop fastener.

11. The method of claim 9 further comprising laundering the device.

12. The method of claim 9 further comprising autoclaving the device.

13. The method of claim 9 wherein the fastener comprises a hoop.

14. The method of claim 13 wherein the hoop is plastic.

15. A patient restraining device for temporarily, safely, and comfortably limiting the mobility of a body portion of a human patient relative to a patient supporting structure, comprising:

a length of non-allergenic fabric having a soft patient engaging surface and an opposed patient non-engaging surface, first and second opposed ends, opposed edges, and a fastener associated with the length for fastening the device to itself and the table and/or stretcher, the edges of the fabric being folded over to present a rolled side margin having a continuously smooth and curved margin face, with the device being autoclavable and sanitizable, thereby hygienically minimizing trauma to the mobility limited body portion, and helping to reduce tissue trauma and the potential for cross-contamination, wherein the device comprises a rigid nylon plastic hoop.

16. The device of claim 15 wherein the fastener is a hook-and-loop fastener.

17. The device of claim 15 wherein the hook portion of the hook-and-loop fastener is disposed on the patient engaging side.

18. The device of claim 15 wherein the device is washable and sanitizable by laundering or band cleaning.

19. A method of restraining a patient relative to a patient supporting structure, the method comprising:

providing a length of non-allergenic fabric having a soft patient engaging surface and an opposed patient non-engaging surface, first and second opposed ends, opposed edges, and a fastener associated with the length for fastening the device to itself, the edges of the fabric being folded over to present a side margin having a continuously smooth and curved margin face, with the device being sanitizable and reusable, placing the patient non-engaging surface against the patient, fastening the device to itself, laundering the device, autoclaving the device, or both laundering and autoclaving the device.

20. The method of claim 19 further comprising fastening the device to itself by fastening a hook-and-loop fastener.

21. The method of claim 19 comprising laundering but not autoclaving the device.

22. The method of claim 19 comprising autoclaving but not laundering the device.

23. The method of claim 19 wherein the fastener comprises a hook-and-loop fastener.

24. The method of claim 23 wherein a hook portion of the hook-and-loop fastener is disposed on the patient-engaging side.

25. The method of claim 19 wherein the fastener comprises a hoop.

26. The method of claim 25 wherein the hoop is plastic.

* * * * *